(12) United States Patent
Weiler et al.

(10) Patent No.: US 6,589,245 B1
(45) Date of Patent: Jul. 8, 2003

(54) INTERFERENCE SCREW

(75) Inventors: Andreas Weiler, Berlin (DE); Michael Strobel, Straubing (DE); André Timmermans, Ruurlo (NL)

(73) Assignee: Karl Storz GmbH & Co. KG (DE)

( * ) Notice: Subject to any disclaimer, the term of this patent is extended or adjusted under 35 U.S.C. 154(b) by 146 days.

(21) Appl. No.: 09/693,381

(22) Filed: Oct. 20, 2000

(30) Foreign Application Priority Data

Oct. 21, 1999 (EP) .............................................. 99121106

(51) Int. Cl.[7] .............................................. A61B 17/86
(52) U.S. Cl. ........................................................ 606/73
(58) Field of Search .......................... 606/73, 65, 66, 606/72, 77

(56) References Cited

U.S. PATENT DOCUMENTS

| | | | |
|---|---|---|---|
| 5,129,904 A | * 7/1992 | Illi ................................. | 606/72 |
| 5,242,447 A | * 9/1993 | Borzone ....................... | 606/73 |
| 5,364,400 A | 11/1994 | Rego, Jr. et al. ............. | 606/72 |
| 5,383,878 A | 1/1995 | Roger et al. .................. | 606/73 |
| 5,688,285 A | 11/1997 | Yamada ....................... | 606/104 |
| 5,951,560 A | * 9/1999 | Simon et al. ................. | 606/73 |
| 5,968,047 A | * 10/1999 | Reed ............................ | 606/72 |

FOREIGN PATENT DOCUMENTS

| | | |
|---|---|---|
| DE | 30 27 138 A1 | 9/1993 |
| DE | 296 21 340 U1 | 5/1998 |
| EP | 0669110 A2 | 8/1995 |
| FR | 2717070 | 10/1995 |
| FR | 2745999 | 11/1997 |

OTHER PUBLICATIONS

OP–Journal, Dec. 1998.

* cited by examiner

Primary Examiner—Todd E. Manahan
(74) Attorney, Agent, or Firm—St. Onge Steward Johnston & Reens, LLC

(57) ABSTRACT

An interference screw serves for anchoring a flexible transplant like a tendon or a ligament in an opening in a bone. The screw has a screw body, a head at one end of said body and a penetrating end at an opposite end of said head and is provided with an outer threading. The outer threading is formed as a sharp threading adjacent to said penetrating end and is formed as a blunt threading in a following region (FIG. 1).

9 Claims, 2 Drawing Sheets

INTERFERENCE SCREW

BACKGROUND OF THE INVENTION

The invention relates to an interference screw for anchoring a tendon or ligament implant in an opening in a bone, the screw having a screw body provided with a head at one end and a penetrating end at the opposite end and said body having an outer threading.

Such interference screws are disclosed in OP Journal 14, 1998, pages 278–284 "Biodegradierbare Interferenzschrauben in der Kreuzbandchirurgie" A. Weiler et al., Georg Thieme Verlag Stuttgart, New York.

Interference screws have the purpose of anchoring a transplant or implant of a tendon or ligament in a bone. A channel is bored into the bone in which the transplant is placed. The interference screw is provided to be screwed into the intermediate space between the transplant and the inner wall of the channel, so that the tendon transplant is clamped between the screw and the wall. The forces acting on such a tendon or ligament, for example the cruciate ligaments in a knee joint, are considerable so that the clamping force must be correspondingly large to guarantee a durable anchor. For this purpose, the interference screw is provided with an outer threading which penetrates into the bone material on the inner side of the channel. At the same time, the outer threading engages with the transplant to be anchored.

The U.S. Pat. No. 5,383,878 discloses an outer threading formed to be a blunt, round threading, which has an approximately sinwave shaped contour about the screw axis. Interference screws having blunt threads are difficult to apply, which is a disadvantage in clinical applications.

The U.S. Pat. No. 5,688,285 discloses an interference screw whose outer threads are provided with sharp edges. The sharp edges can cut into the tendon transplant when being screwed in and weaken the transplant to the point that it releases from the anchoring position under load.

For this reason, such interference screws are mainly employed in the so-called BTB technique (bone-tendon-bone). Here, the tendon transplant is surrounded by a piece of bone in the region where it engages with the sharp threading of the inference screw, so that the interference screw penetrates the end of the tendon surrounded by the bone material on the one hand and the bone material at the inner wall of the channel on the other hand.

An object of the present invention is to provide an interference screw which allows a simple and secure anchoring of a tendon or ligament transplant.

SUMMARY OF THE INVENTION

According to the present invention, the object is achieved in that the outer threading of the screw body is formed to be sharp in an area adjacent to the penetrating end and is formed with a blunt threading in the following regions.

When applying the interference screw, the sharp threads adjacent the penetrating end clearly define an entrance path for the following blunt sections of the threading. Approximately complementary screw line paths are cut into the inner side of the channel. The blunt regions of the threading can then be simply screwed into these cut lines, where the blunt regions of the threading then provide sufficient compression to anchor the tendon transplant to the inner side of the channel. In this manner, the interference screw can be simply mounted and is properly guided. A further advantage is that it is ensured that the transplant tissue is not impaired, i.e. not severed or separated in the region of the blunt threading.

In a further embodiment of the present invention, at least one thread winding is formed to be sharp. By providing at least one winding of the threading to be a sharp, cutting thread it is guaranteed that a guide line or guide path is cut about the entire circumference of the channel wall, in which the subsequent blunt regions of the threading can exactly follow.

In at least one embodiment of the present invention, the screw body is tapered at the penetrating end and the sharp threads extend to about the position of maximum outer diameter of the outer threading.

This feature has the advantage that the tapered end of the interference screw can be placed in the free space between the end of the tendon and the channel and can be correctly aligned for application. Since the tendon material has a certain compressibility, the material in the region of the threads at the penetration end can be displaced to the side, so that the danger of impairment by the threading is further reduced. Corrections in which the screw is removed and then screwed in again are thus no longer necessary. It is also ensured that the sharp threads extending up to the maximum core diameter are able to cut the entry path in the inner wall of the bone channel. The handling is thus further simplified.

In a further preferred embodiment of the present invention, the transition from sharp to blunt threads is gradual. The feature has the advantage that the guidance of the following blunt threads into the spiral paths previously cut by the sharp threads in the inner wall of the channel is very smooth.

In a further embodiment of the present invention, the outer threading is formed to be buttress threads. The feature has the advantage that the forward flanks of the tooth profile can penetrate into the material rather softly. With the relatively compressible tendon material, it is correspondingly radially shifted or compressed without negative effects on the transplant. Both the bone material and the tendon material have a certain resiliency, so that the material is pushed back to the region of the back flanks and forms a mechanically rigid, closed connection with the interference screw.

In a further embodiment of the present invention, the interference screw is made of biodegradable material. This feature has the advantage that with time the bone material grows into the space previously occupied by the screw material. After time, this ensures a secure seating of the tendon transplant, because an organic growth with the tendon transplant takes place. A loosening between the interference screw and the anchored tendon transplant due to loads or degenerative deformations is therefore excluded and a durable secure seating is guaranteed. This also opens the possibility of providing new borings, if revision is necessary, to anchor another or different transplant at the same bone region, since bone material has again accumulated through subsequent growth which can be bored again.

In a further embodiment of the present invention, the screw body is formed as a hollow body and in a further embodiment is preferably provided with several perforations.

This feature has the advantage that the formation of a three-dimensional bone structure in the region of the screw is further promoted by the perforations. Bone material can grow into the interior of the hollow body through the perforations or can grow together and form an intimate connection with bone material already present in the interior space of the hollow body, whether this is bone slurry or pieces of bone. This process can run parallel to the biological degradation of the material of the screw, so that a secure seating of the transplant is always ensured and with time, more and more natural bone material is formed in the region of the transplant. The form, distribution and the number of perforations are selected such that sufficient stability of the hollow body is retained, even though numerous openings for growth are present.

In a further embodiment of the present invention, the perforations are provided between the windings of the threads. The feature has the advantage that the windings can retain a continuous spiral contour, which simplifies a smooth screw mounting of the interference screw. The perforations for bone tissue growth are then present in the intermediate spaces in the actual screw body.

It will be understood that the above-mentioned features and those to be discussed below are applicable not only in the given combinations, but may be present in other combinations or be taken alone without departing from the scope of the present invention.

BRIEF DESCRIPTION OF THE DRAWINGS

The invention will be discussed in more detail below in conjunction with selected embodiments and the attached drawings.

DETAILED DESCRIPTION OF PREFERRED EMBODIMENTS

Figure 1:
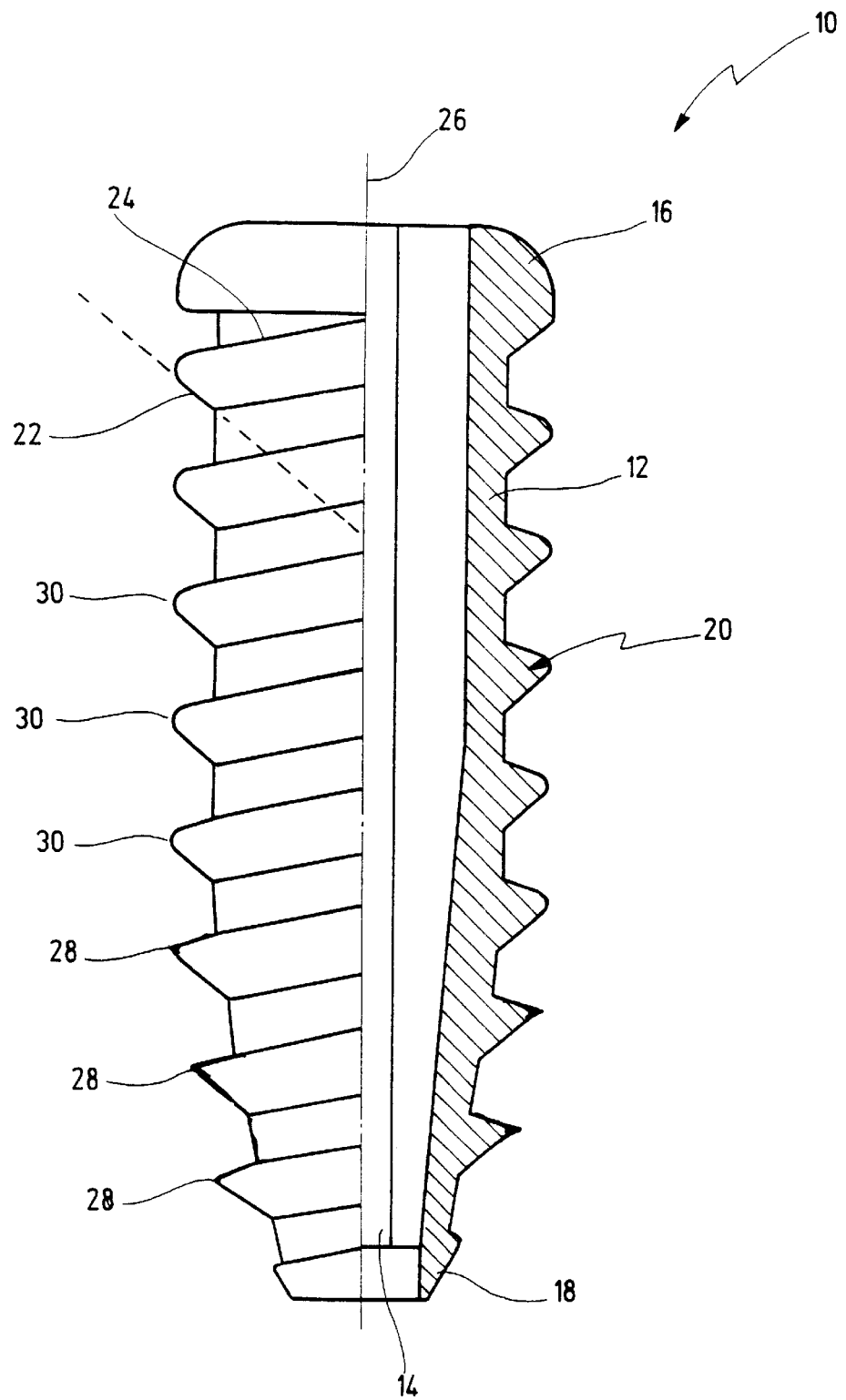
FIG. 1 shows a side view of an interference screw according to the present invention, where the right half of the figure is in cross-section.

An interference screw is shown in FIG. 1 and generally designated with the reference numeral 10. The interference screw 10 comprises a hollow screw body 12 having a head end 16 and a penetrating end 18. The approximately hollow cylindrical screw body 12 is tapered in the region of the penetrating end 18.

A continuous channel 14 extends through the screw body 12 from the head 16 to the penetrating end 18, whose cross-section at least in the region of the head 16 is formed with a sexangular contour. An outer thread 20 is provided on the outside of the screw body 12, which extends from the penetrating end 18 to the head 16.

The outer threading 20 in the present embodiment has a profile of a buttress threading. The respective forward flanks 22, facing the penetrating end 18, are displaced by an angle of about 45° degrees with respect to the center axis 26 of the screw 10, as shown in the left half of FIG. 1 with a dashed line. The other flanks 24, viewed from the head 16 to the penetrating end 18, run at an inclination of about 15° degrees downwardly, measured with respect to a plane perpendicular to the axis 26. The flanks 22 and 24 are joined at a sharp edge 28 in the region of the penetrating end 18 up to about the maximum core diameter of the screw body 12. In the following regions, the flanks 22 and 24 are respectively joined with blunt edges 30.

This results in a first region of the outer threading 20 near the penetration end 18 having sharp threads. A second region follows which extends to the head 16 and has blunt threads.

The interference screw 10 shown in FIG. 1 consists of a biocompatible material, namely titanium.

Figure 2:
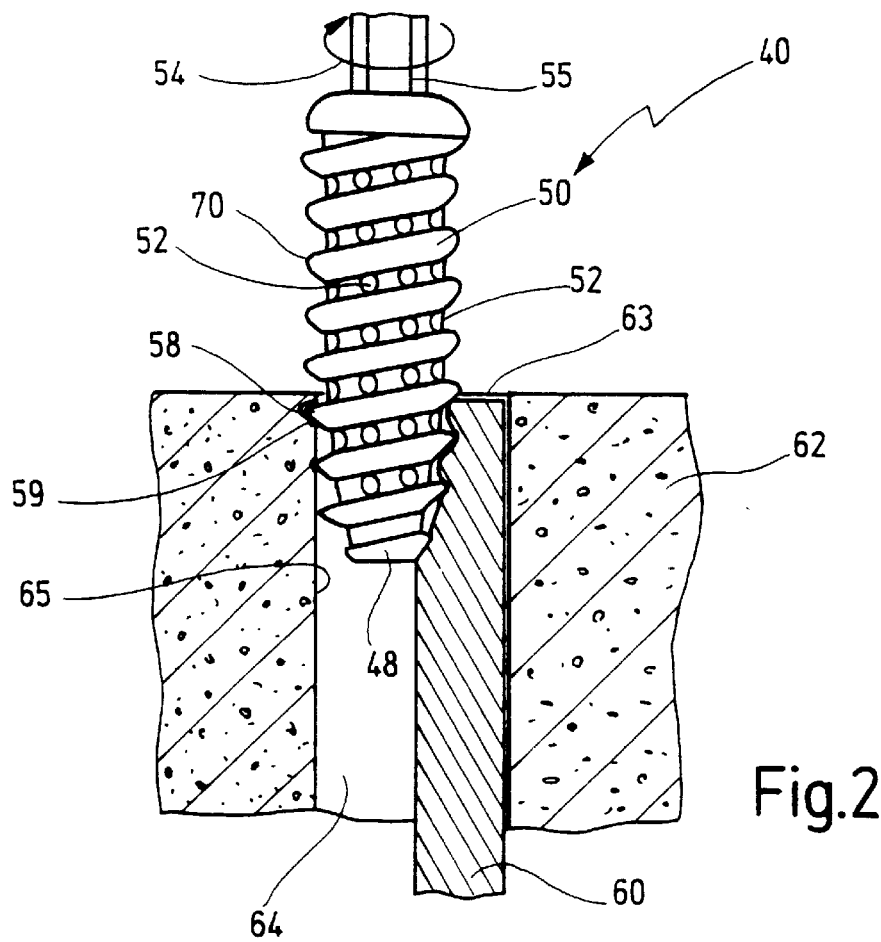
FIG. 2 shows a partial cross-section of a further embodiment of an interference screw, which is additionally provided with perforations and where the illustration shows the interference screw being driven into a channel in the bone with a tool to anchor a transplant.
Figure 3:
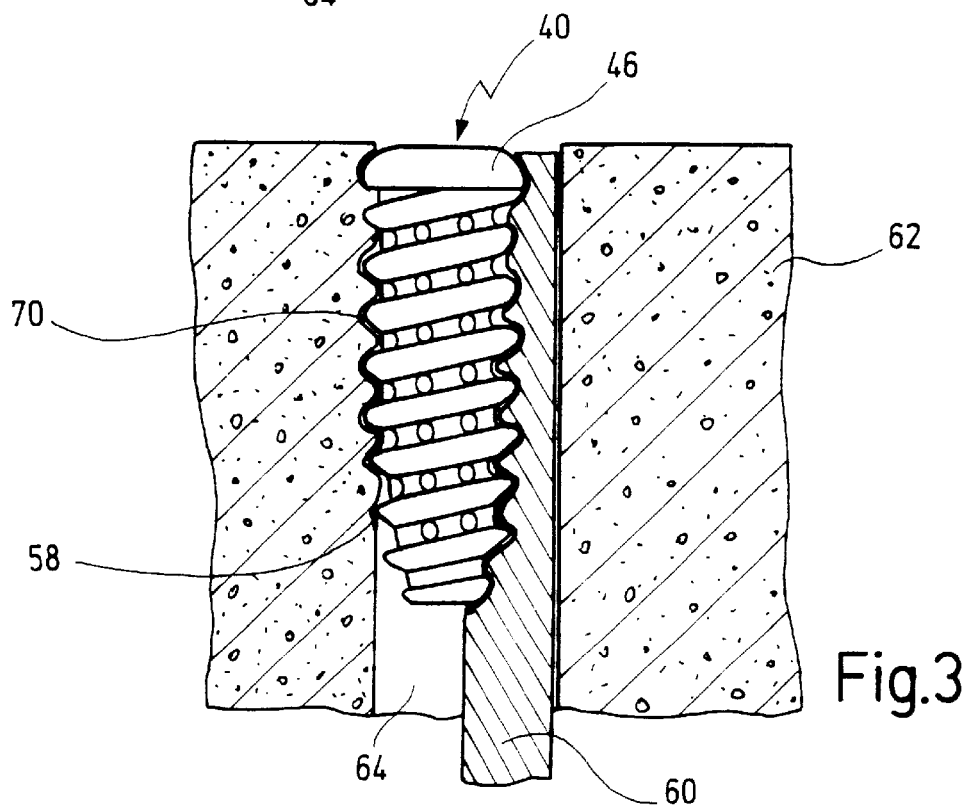
FIG. 3 shows an illustration comparable to FIG. 2 after complete insertion of the interference screw with the anchored transplant.

A further embodiment of an interference screw 40 is shown in FIGS. 2 and 3, which with respect to the configuration of the outer threading 50 is identical with the interference screw 10 described in FIG. 1. The interference screw 40 thus also comprises a head 46 and a penetrating end 48.

In contrast to the embodiment of FIG. 1, the interference screw 40 is made of a biodegradable material and in addition is provided with numerous perforations 52 between the windings of the outer threading 50. Examples of biodegradable material include polycaprolactone, poly(L-lactide), polyglcol, poly(D,L-lactide), poly(D,L-lactide-co-glycol), poly(D,L-lactide-co-caprolactone), polydioxanone, copolyoxalate, polycarbonate, for example polyglycol-co-trimethylencarbonate, and poly(glutamine-co-leucine).

The perforations 52 in this embodiment comprise circular openings, so that a connection from the exterior to the interior of the screw 40 also provided as a hollow body is present through these openings.

The purpose of this configuration will be discussed in conjunction with the operation of the interference screw 40 for anchoring a tendon transplant 60 and is identical to the operation of the embodiment shown in FIG. 1 with a screw 10 of metal. This is based on the knowledge that biodegradable interference screws have the same initial high anchoring stability as do metal screws.

The procedure for anchoring with an interference screw will now be described. An opening 63 in the form of a bore channel 64 is provided in the bone 62, onto which a tendon or ligament transplant 60 is to be anchored. The diameter of the channel 64 is selected such that the transplant 60 or an end thereof can be inserted in the channel.

When replacing a cruciate ligament, corresponding channels 64 are provided in both the femur and the tibia and the transplant is anchored at both locations as for example shown in FIG. 1 of the above-mentioned article in OP Journal 14 (1998), et seq.

For simplicity sake the anchoring of only one end of the transplant 60 is illustrated in FIG. 2, while a corresponding other end is anchored in the same manner. After inserting the transplant 60 into the channel 64, the screw 40 is placed such that the penetrating end 48 is located between the inner wall 65 of the channel 64 and the outer end of the transplant 60. This placement and insertion is easier because of the tapering in the region of the penetrating end 46.

A tool 54 is applied to the head 64, whose outer contour corresponds to the cross-sectional contour of the inner channel, for example having a sexangular cross-section. The interference screw 40 is screwed in by rotating the tool 54 as shown by the arrow 55.

FIG. 2 shows the situation in which the sharp edges 58 of the outer threading 50 in the region of the penetrating end 48 just begin to engage with the inner wall 65 of the channel 64, i.e. with the bone material. By rotating the screw 40, the sharp edges 58 cut a relatively narrow, sharply contoured, spiral path in the inner wall of the channel 64. At the location where the threading 50 has the sharp edges 58, i.e. in the region of about the first three windings, the forward flanks of the threading 50 are urged into the material of the tendon transplant 60. This is performed without damaging the transplant material, which is aided by the fact that the penetrating end 48 is tapered.

With further rotation of the screw 40, the following blunt windings pass smoothly into the inner threading 59 having been precut by the sharp edges 58 in the inner wall 65. The inner winding 59 is expanded and also provides the actual radial compression. The blunt windings penetrate deeply and firmly into the material of the tendon transplant 60 as is seen in FIG. 3 on the right hand side. The material of the tendon or ligament transplant 60 is not damaged by the outer winding 50 because the engagement of the outer winding 50 with the transplant material at high compression takes place substantially in the region of the blunt windings.

The interference screw 40 can be applied in simple manner and provides sufficient pressure for a secure anchoring of the transplant 60.

The bone material can now grow with time into the interior of the screw 40 through the perforations 52. The interior can be filled with bone material, for example bone slurry or bone pieces, which for example have been removed from the pelvic crest region. A solid structure of bone material soon forms in the interior of the screw, for example after six to eight weeks.

The material of the interference screw being biodegradable, it is absorbed with time, i.e. disappears with time, so that the resulting spaces are again grown over with bone material. With this advantageous configuration, the time for biodegradation need not be correlated with the rate of bone growth, which can be very much faster because the perforations 52 provide sufficient space for the bone material even before and also during the degradation to form a three-dimensional interconnected bone structure. This offers considerably improved possibilities, specially with respect to revision work.

What is claimed is:

1. An interference screw for anchoring a flexible transplant in an opening in a bone, comprising:

a screw body, a head at one end of said body, a penetrating end at an opposite end of said head end, an outer threading provided on an outer side of said screw body, wherein said outer threading is formed as a sharp threading adjacent to said penetrating end, and is formed as a blunt threading in a following region following said sharp threading, and wherein said sharp threading extends to a maximum core diameter of said screw body, thereby cutting entrance paths for said blunt threading into a wall of said opening within said bone.

2. The interference screw of claim 1, wherein at least one 360° thread winding of said body is formed to be sharp.

3. The interference screw of claim 1, wherein said penetrating end is tapered, and wherein said sharp threading extends from said penetrating end up to about where a maximum outer diameter of said outer threading in said screw body is reached.

4. The interference screw of claim 1, wherein a transition from said sharp to said blunt threading is smooth.

5. The interference screw claim 1, wherein said outer threading is formed as a buttress threading.

6. The interference screw of claim 1, wherein said screw is made of a biodegradable material.

7. The interference screw of claim 1, wherein said screw body is formed as a hollow body.

8. The interference screw of claim 1, wherein said screw body is provided with several perforations.

9. The interference screw of claim 8, wherein said perforations are provided between windings of said outer threading.

* * * * *